United States Patent [19]
Martin

[11] 3,955,572
[45] May 11, 1976

[54] DISPOSABLE CAP AND FLOAT ASSEMBLY

[75] Inventor: Gordon D. Martin, Mundelein, Ill.

[73] Assignee: Aeros Instruments, Inc., Northbrook, Ill.

[22] Filed: Dec. 20, 1974

[21] Appl. No.: 534,844

[52] U.S. Cl. .............................. 128/275; 248/312
[51] Int. Cl.² .................................... A61F 5/44
[58] Field of Search .......... 128/275, 276, 272, 295; 248/312, 311, 215, 240; 211/74, 81

[56] References Cited
UNITED STATES PATENTS

| | | | |
|---|---|---|---|
| 1,774,840 | 9/1930 | Otto | 248/312 |
| 2,754,009 | 7/1956 | Kennedy | 248/312 X |
| 3,222,023 | 12/1965 | Schweitzer | 211/74 X |
| 3,339,814 | 9/1967 | Carbine | 248/312 X |
| 3,548,827 | 12/1970 | Abel | 128/275 |
| 3,653,624 | 4/1972 | Abel | 128/275 |
| 3,782,414 | 1/1974 | Holbrook | 128/275 X |

Primary Examiner—John D. Yasko
Attorney, Agent, or Firm—Coffee and Sweeney

[57] ABSTRACT

A disposable cap and float assembly for a drainage container or receiver in a vacuum system for receiving drainage from the body of a patient after wounding of or surgery performed on the patient or for other liquid withdrawal procedures. The assembly includes a bifurcated bracket mountable on a wall or in a floor stand and which removably retains the drainage receiver in the vertical direction. A cap for sealing the drainage receiver is vertically downwardly disposed over the top of the drainage receiver while retained in the bifurcations of the bracket for horizontally retaining the drainage receiver between the bifurcations of the bracket. The cap is snap fit over the bracket to retain the cap to the bracket and hold the receiver or container in the bracket. A float closes a vacuum passage in the cap when the receiver is filled, preventing the suction of drainage into the vacuum system.

12 Claims, 9 Drawing Figures

DISPOSABLE CAP AND FLOAT ASSEMBLY

BACKGROUND OF THE INVENTION

The present invention relates to a disposable cap and float assembly for a drainage receiver for receiving drainage from the body of a patient after the wounding of or surgery performed on the patient or for other liquid withdrawal purposes. In the past, various designs for drainage receivers have been proposed. Previously known are drainage receivers in the form of disposable flexible plastic liners positioned in a canister as shown, for example, in U.S. Letters Pat. No. 3,685,517. Being flexible, such liners are subject to collapse unless held against the canister by vacuum, necessitating a separate vacuum port. If care in assembly of the liner in the canister is not exercised, the liner itself may plug the vacuum port causing the liner to collapse. Such plastic liners also are subject to vacuum or drainage leaks if the liner is snagged or if it is inadequately sealed during manufacture. Therefore, the use of rigid receivers often is more desirable.

Rigid receivers are readily sterilized for reuse, but the cap assemblies of these receivers, due to their configurations, are more difficult to sterilize for reuse than the receiving containers. Where steam sterilization is utilized, the parts must be made of a material which will not be adversely affected by the steam temperature, or sterilization must be accomplished by a low temperature chemical sterilization method which not only is expensive but can pose physical dangers to personnel. Therefore, it is desirable that the cap and float assembly of the rigid drainage receiver be disposable. This invention is directed to providing a new and improved disposable cap and float assembly for use in drainage receivers, or the like, particularly in the medical field.

SUMMARY OF THE INVENTION

The assembly of the present invention includes a bifurcated bracket mountable on a wall or in a floor stand and a disposable cap for sealing a rigid drainage receiver. The cap is vertically downwardly disposed over the bifurcations of the bracket and the drainage receiver is retained in the bracket.

Hereinafter, the plane of the bifurcations of the bracket will be designated as the horizontal plane, and vertical will designate a direction 90° to the plane of the bifurcations whether they are in fact positioned parallel to the horizon or not.

Means for horizontally retaining the drainage receiver between the bifurcations of the bracket and means for retaining the cap vertically onto the bracket are included. First and second tubular portions form first and second passages vertically through the cap to admit drainage from the patient's body and allow the evacuation of the drainage receiver. A float shutoff valve is positioned over an interference fit portion on the bottom of the first tubular portion so as to seal vertically upward against a shutoff seat surface on the first tubular portion when the drainage receiver becomes filled with fluid.

An object of the present invention is to provide a cap and float assembly of the character described which is sufficiently inexpensive as to be disposable, thus obviating the difficult sterilization for reuse of this portion of the drainage receiving assembly.

It also is an object of the invention to provide a float shutoff valve so designed as to allow substantially all of the drainage receiver capacity to be utilized.

Additional objects, advantages and features of the invention will be apparent to those skilled in the art upon consideration of the complete specification.

DESCRIPTION OF THE PREFERRED EMBODIMENT

Figure 1:
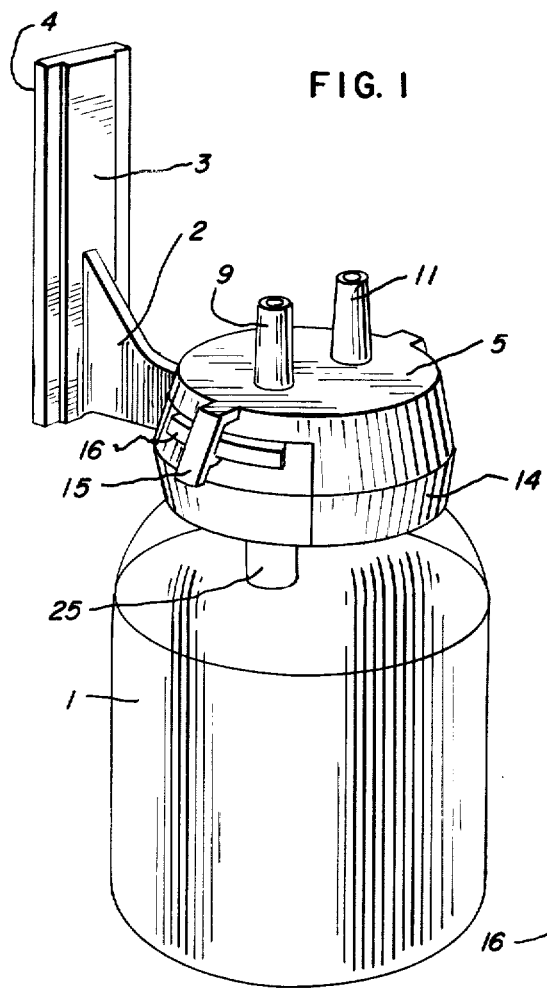
FIG. 1 is a perspective view of the cap and float assembly of the present invention on a drainage receiver.

The disposable cap and float device of the present invention is shown completely assembled in FIG. 1 on a drainage receiver 1. A bifurcated bracket 2, in the preferred embodiment, is illustrated with a mounting portion 3 which may be equipped with an adhesive surface 4 for mounting the bifurcated bracket to a wall, bed panel or other convenient surface.

Figure 3:
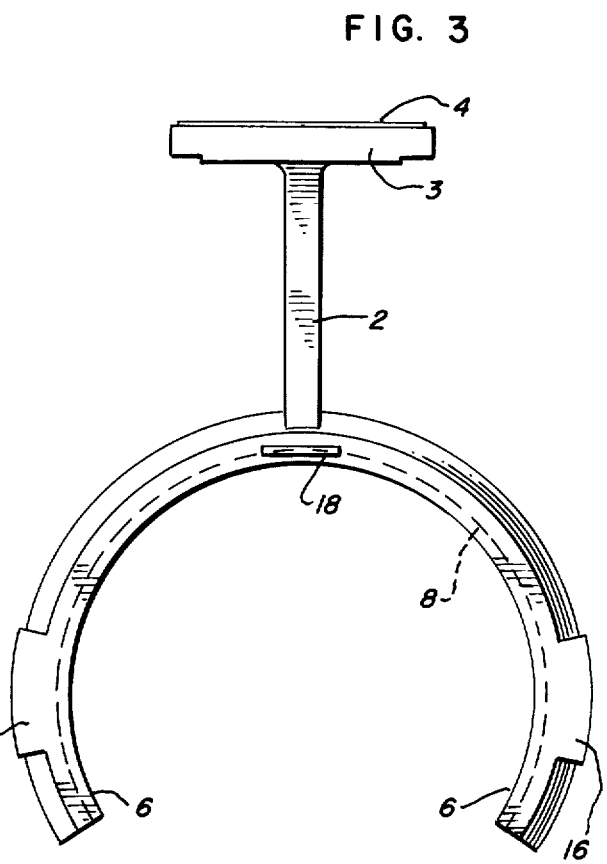
FIG. 3 is a top plan view of the bifurcated bracket.
Figure 2:
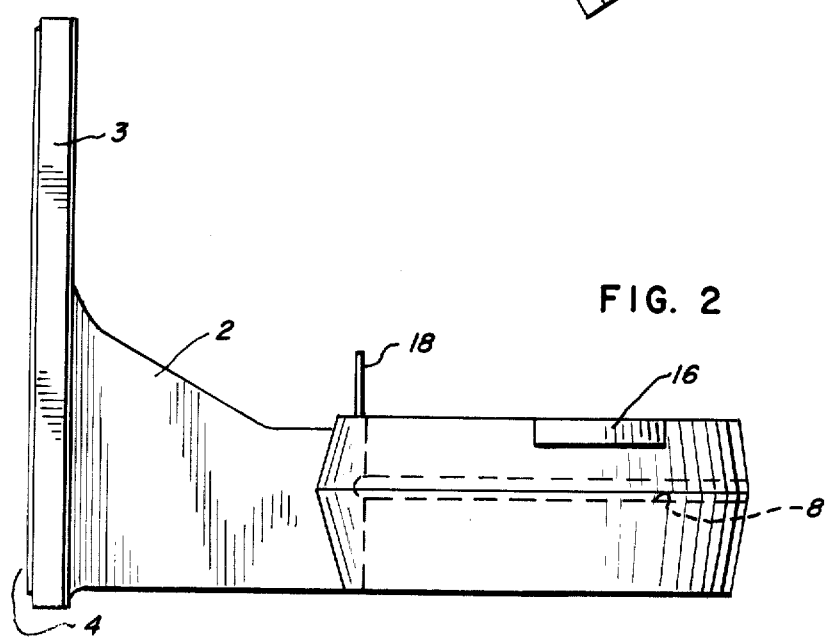
FIG. 2 is a side elevational view of the bifurcated bracket.

The bifurcated bracket 2, as described in greater detail hereinafter, is equipped with lugs, tabs, grooves and other similar means to vertically retain drainage receiver 1 between bifurcations 6. In FIGS. 2 and 3, the means to vertically retain the drainage receiver 1 is shown by hidden lines as a groove 8 which engages a ring (not shown) on the drainage receiver.

The cap 5 is so designed as to be vertically downwardly positionable over the drainage receiver 1 and the bifurcations 6 to seal the drainage receiver and to fasten the cap 5 to the bifurcated bracket 2. As described hereinafter, this also retains the drainage receiver horizontally in the bracket.

Figure 4:
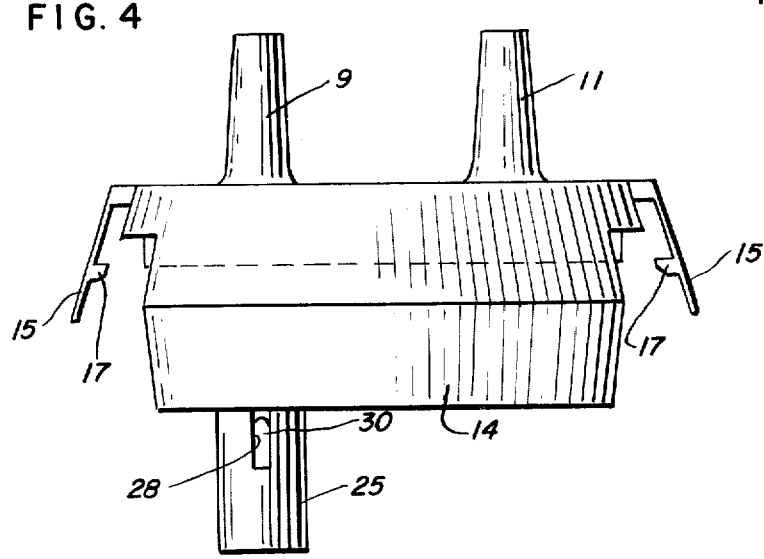
FIG. 4 is a front elevational view of the cap, showing the extended arcuate skirt and locking tabs.
Figure 5:
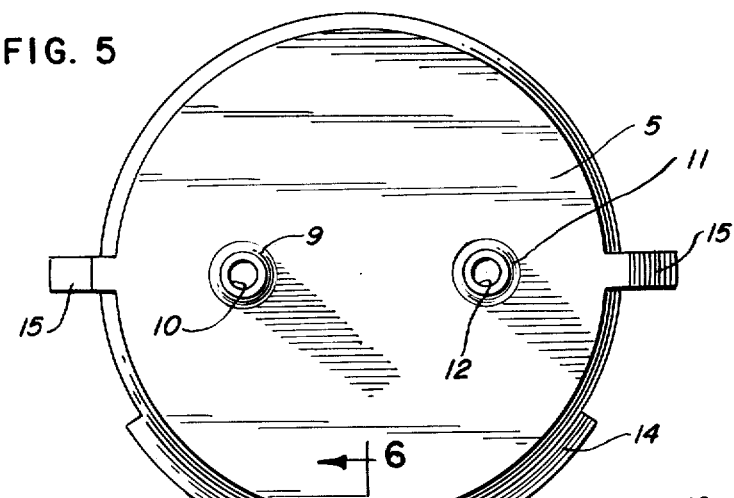
FIG. 5 is a top plan view of the cap, showing the first and second tubular openings and positioning of the extended arcuate skirt.
Figure 7:
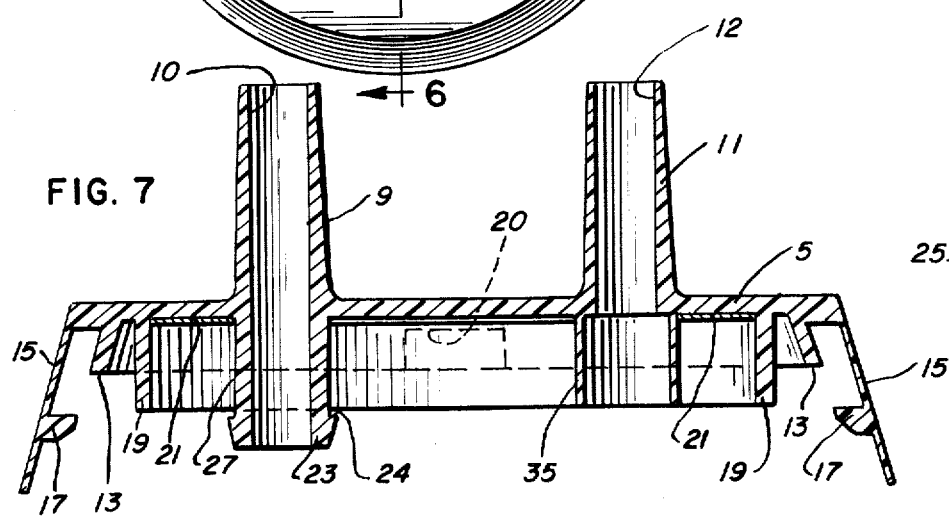
FIG. 7 is a vertical sectional view of the cap taken along line 7—7 of FIG. 5.
Figure 8:
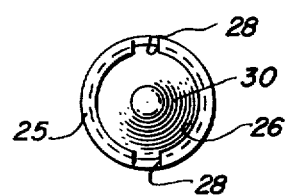
FIG. 8 is a top plan view of the movable float shutoff valve member.

Herein, the plane of the bifurcations 6 of the bifurcated bracket 2 will be designated as the horizontal plane, and vertical will designate a direction at 90° to the plane of the bifurcations 6. It will be understood by those skilled in the art that the entire assembly could be mounted such that the plane of bifurcations 6 is not in fact positioned parallel to the horizon. Cap 5, as best illustrated in FIGS. 4, 5 and 7, has a first tubular portion 9 forming a first passage 10 through cap 5 and a second tubular portion 11 forming a second passage 12 through cap 5. Tubular portion 9 is the inlet and tubular portion 11 is the vacuum connection.

The drainage receiver 1 is positioned horizontally between the bifurcations 6 of bracket 2 by horizontal movement of the lip of the drainage receiver through the front opening between the bifurcations in the direction of arrow A (FIG. 3). The receiver lip seats in the bracket groove 8. The opening between the bifurcations 6 is less than 180° to provide a snap connection with the round receiver lip.

Figure 6:
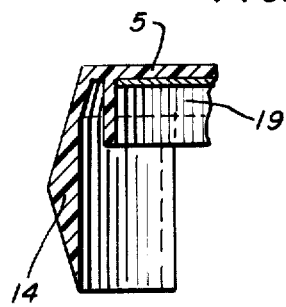
FIG. 6 is a broken vertical sectional view of the cap, showing a cross-section of the extended arcuate skirt, taken substantially along line 6—6 of FIG. 5 in the direction of the arrows.

The cap 5 then is positioned downwardly onto the bracket and drainage receiver to hold the receiver in the bracket. In the preferred embodiment this is accomplished in part by a first annular ring 13, shown in FIG. 7, which extends downwardly from cap 5 and which has an extended arcuate skirt portion 14, shown in FIGS. 4, 5 and 6. Upon the vertically downward disposition of cap 5 during assembly of the unit, skirt 14 is positioned between the distal ends of bifurcations 6 and, thereby, with bifurcations 6, completely encircles drainage receiver 1. Means for holding cap 5 vertically onto bracket 2 in the assembled position are provided by a pair of diametrically disposed flexible locking tabs 15 depending from the sides of cap 5. A pair of complementary outwardly projecting tabs 16 are provided on the outside of each bifurcation 6. The projections 17 of the flexible locking tabs 15 of the cap 5 snap over the tabs 16. Angular rotation in the horizontal plane as well as horizontal movement of the receiver opposite that of arrow A (FIG. 3) is prevented by positioning a tab 18, advantageously located at the rear junction of the bifurcations 6. This tab seats in a notch 20 (FIG. 7) on a second annular ring 19 disposed within the first annular ring 13 on the underside of cap 5. An annular sealing surface 21 (FIG. 7) is disposed within second annular ring 19 for forming a vacuum seal against the top rim of the drainage receiver 1.

Figure 9:
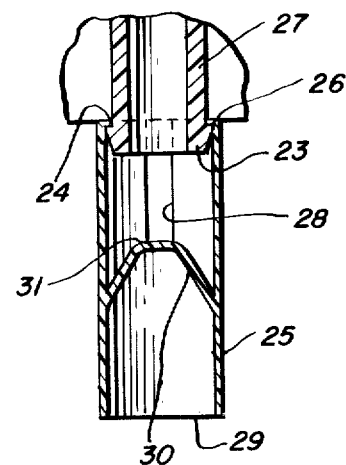
FIG. 9 is a vertical sectional view taken along line 9—9 of FIG. 8.

The first tubular portion 9 extends below cap 5 (see FIG. 7) forming a tubular protruding element 27 and terminating with an interference fit portion 22 in the form of a shoulder 24. Interference fit portion 22 has a lower annular seat forming a shutoff surface 23. The outer periphery of the interference fit portion is beveled upwardly and outwardly so as to form the shoulder 24 around tubular element 27 to retain a float shutoff valve 25 in operating position by engaging a lip 26 (FIG. 9) on the valve 25. Float shutoff valve 25 is so dimensioned that fluid flowing into the drainage receiver 1 will cause it to float upward around tubular element 27, but interference fit portion 22, by means of shoulder 24 engaging lip 26, will retain the float valve 25 in position about the tubular element 27 when no fluid is present in drainage receiver once the lip 26 of valve 25 is snap fit over interference fit portion 22.

To drain fluid from a patient, the drainage receiver 1 is evacuated through the first passage 10 through cap 5 by means of a vacuum tube placed over the first tubular portion 9. The float shutoff valve 25 has longitudinal slots 28 which allow the free flow of gas past valve 25 and out first passage 10. With vacuum applied through passage 10, drainage from the patient's body enters the drainage receiver 1 through second passage 12 through cap 5 and through slots 28 past valve 25.

As the drainage receiver 1 begins to substantially fill, valve 25 is floated upward by the fluid drained from the patient's body. Valve 25 has an open bottom 29 and a conical-shaped divider 30 forming a bulb-type float cavity. By virtue of slots 28 and because bottom 29 is open, as the drainage receiver is evacuated, the space above and below divider 30 is maintained at the same pressure as the balance of the interior of drainage receiver; therefore, valve 25 may be made of a plastic material without danger of valve 25 rupturing as may occur where a sealed air space is present.

Conical divider 30 may thus be fitted at its apex 31 with a deformable resilient rubber seal which may be retained in place by suitable means. As the drainage receiver becomes filled, valve 25 is floated upward and closes at apex 31 contacting seat surface 23 preventing further filling of receiver 1 and eliminating the possibility of fluid being sucked into the hospital vacuum system since the bottom of tubular portion 27 is below that of the vacuum passage 12, with an extension tube 35 (FIG. 7) therebelow. Also, since the first passage 10 remains evacuated after seal 31 contacts surface 23, the shutoff action is aided by the vacuum and valve 25 remains firmly closed. The design of valve 25 is advantageous because the relatively small vertical height of valve 25 allows the volume of receiver 1 to be more completely utilized.

I claim:

1. A disposable cap assembly and drainage receiver combination, comprising: a drainage receiver having an open upper mouth a bifurcated bracket having means to vertically retain, the drainage receiver between the bifurcations, a cap portion for sealing the open mouth of the drainage receiver, the cap portion being vertically downwardly positionable onto the top of the drainage receiver, and complementary vertically engaging surface means on the bifurcated bracket and the cap portion for retaining the cap portion vertically onto the bracket and to hold the drainage receiver between the bracket and cap portion.

2. The assembly of claim 1 wherein the bifurcated bracket includes means for mounting the same onto a wall, bed panel or the like.

3. The assembly of claim 1 including fluid passage means through said cap portion, said passage means including a first tubular portion forming a fluid inlet through the cap into the drainage receiver and a second tubular portion providing an outlet for gases from the drainage receiver, said first tubular portion including a shutoff seat surface and an interference fit portion, and including a float shutoff valve member disposed over the interference fit portion so as to vertically seal upwardly against the shutoff seat surface upon the drainage receiver becoming filled.

4. The assembly of claim 1 wherein said cap portion has a downwardly extending arcuate skirt portion which, upon its vertically downwardly positioning onto the bifurcated bracket, is disposed between the distal ends of the bracket bifurcations forming a continuation thereof.

5. The assembly of claim 1 wherein said complementary engaging surface means on the bracket and the cap portion includes a projecting tab on at least one of the bifurcations of the bracket and a flexible locking tab on the cap portion for snap fit over said projecting tab to hold the cap portion vertically onto the bracket.

6. The assembly of claim 1 wherein said complementary engaging surface means includes a vertically protruding tab on one of said bracket and said cap portion and a recess for receiving said tab on the other of said bracket and said cap portion for horizontally holding the bracket and cap portion with the drainage receiver therebetween.

7. The assembly of claim 6 wherein said complementary engaging surface means on the bracket and the cap portion includes a projecting tab on at least one of the bifurcations of the bracket and a flexible locking tab on the cap portion for snap fit over said projecting tab to hold the cap portion vertically onto the bracket.

8. A disposable cap assembly and drainage receiver combination, comprising: a drainage receiver having an open upper mouth a bracket portion having means for mounting the same onto a wall, bed panel or the like and means for receiving the drainage receiver by horizontal positioning of the receiver onto the bracket, a cap portion for sealing the open mouth of the drainage receiver, the cap portion being vertically downwardly positionable onto the top of the drainage receiver, and complementary horizontally locking surface means on the bracket portion and cap portion to horizontally hold the drainage receiver on the bracket.

9. A disposable cap assembly and drainage receiver combination, comprising:

a drainage receiver having an open upper mouth;

a bifurcated bracket adapted to accept the drainage receiver horizontally thereinto between the bifurcations of the bracket with means to vertically retain the drainage receiver between the bifurcations, an outwardly projecting tab formed on the outside of each bifurcation of the bracket, a vertically extending tab formed on the bracket, and means on the bracket to mount the same to a wall or other appropriate supporting means; and a cap for sealing the open mouth of the drainage receiver and holding the drainage receiver between the bifurcations of the bracket, said cap being vertically downwardly positionable over the drainage receiver and the bifurcations of the bracket and including a flexible locking tab to engage each of the projecting tabs on the bracket bifurcations to hold the cap vertically onto the bracket in sealing engagement with the drainage receiver, a notch for receiving the vertically extending positioning tab of the bracket to hold the cap horizontally onto the bracket, a downwardly extending arcuate skirt which, upon the vertically downwardly positioning of the cap onto the bracket, is positioned between the distal ends of the bracket bifurcations forming a continuation thereof and preventing horizontal movement of the drainage receiver outwardly from between the bifurcations, an annular sealing surface disposed on the underside of the cap for forming a vacuum seal against the top of the drainage receiver, and liquid passage means through the cap.

10. The assembly of claim 9 wherein said liquid passage means through said cap portion includes a first tubular portion forming a fluid inlet through the cap into the drainage receiver and a second tubular portion providing an outlet for gases from the drainage receiver, said first tubular portion including a shutoff seat surface and an interference fit portion, and including a float shutoff valve member disposed over the interference fit portion so as to vertically seal upwardly against the shutoff seat surface upon the drainage receiver becoming filled.

11. A cap and float shutoff valve means for a drainage receiver, comprising: a first passage through the cap forming an inlet for liquid therethrough into the drainage receiver, a second passage through the cap forming an outlet for gases from the drainage receiver to a vacuum system or the like, a tubular portion in communication with said first passage and extending downwardly from a cross wall of the cap which is in sealing engagement with the top of the drainage receiver, a shutoff valve seat surface about the lower end of said tubular portion, an interference fit means on the outside of said tubular portion, and a float shutoff valve member disposed over the interference fit portion for sealing engagement with said seat surface upon upward vertical movement thereof upon the drainage receiver becoming filled.

12. The assembly of claim 11 wherein said valve member comprises a generally tubular device telescopingly receivable over the tubular portion in communication with said first passage means and having interengaging surface means on the inside thereof for engaging the interference fit portion on said tubular portion, and an upwardly generally conically shaped divider on the inside of said tubular valve member intermediate the ends thereof for seating against said shutoff valve seat surface, with that portion of the tubular valve member below the conical divider forming the float portion of the valve thereby providing for maximum filling of the drainage receiver.

* * * * *